United States Patent
Seress et al.

(10) Patent No.: US 6,500,651 B1
(45) Date of Patent: *Dec. 31, 2002

(54) METABOLIC CONTROLLED FERMENTATION PROCEDURE FOR THE MANUFACTURE OF LOVASTATIN HYDROXY ACID

(75) Inventors: Péter Seress, Debrecen (HU); Gábor Balogh, Debrecen (HU); Antal Oláh, Debrecen (HU); László Cséke, Debrecen (HU)

(73) Assignee: Biogal Gyogyszergyar Rt., Debrecen (HU)

( * ) Notice: Subject to any disclaimer, the term of this patent is extended or adjusted under 35 U.S.C. 154(b) by 0 days.

This patent is subject to a terminal disclaimer.

(21) Appl. No.: 09/424,131

(22) PCT Filed: Mar. 19, 1999

(86) PCT No.: PCT/HU99/00021

§ 371 (c)(1),
(2), (4) Date: Apr. 5, 2000

(87) PCT Pub. No.: WO99/49072

PCT Pub. Date: Sep. 30, 1999

(30) Foreign Application Priority Data

Mar. 20, 1998 (HU) .......................................... P98-00619

(51) Int. Cl.⁷ ............................ C12P 17/06; C12P 17/02
(52) U.S. Cl. ...................... 435/125; 435/123; 435/171; 435/256.1
(58) Field of Search ................................ 435/125, 171, 435/123, 256.1; 436/265.1

(56) References Cited

U.S. PATENT DOCUMENTS

| 4,294,846 | A | | 10/1981 | Albers-Schonberg et al. |
|---|---|---|---|---|
| 4,294,926 | A | | 10/1981 | Monaghan et al. |
| 4,319,039 | A | | 3/1982 | Albers-Schonberg et al. |
| 4,342,767 | A | | 8/1982 | Albers-Schonberg et al. |
| 4,420,491 | A | | 12/1983 | Albers-Schonberg et al. |
| 4,945,048 | A | | 7/1990 | Uchihori et al. |
| 5,316,776 | A | | 5/1994 | Annuk et al. |
| 5,403,728 | A | * | 4/1995 | Jekkel et al. ............... 435/125 |
| 5,494,808 | A | | 2/1996 | Fu |
| 6,197,560 | B1 | * | 3/2001 | Seress et al. ............... 435/125 |

FOREIGN PATENT DOCUMENTS

| DE | 4402591 | 10/1994 |
|---|---|---|
| GB | 2046737 | 11/1980 |
| WO | 97 05269 | 2/1997 |

* cited by examiner

Primary Examiner—Herbert J. Lilling
(74) Attorney, Agent, or Firm—Kenyon & Kenyon

(57) ABSTRACT

A method for producing mevinolin by a microorganism in a fermentation process having a seed culture stage and a main fermentation stage, including
a) cultivating a microorganism biomass in the seed culture stage to produce an inoculum;
b) transferring the inoculum into a fermentation medium in the main fermentation stage; and,
c) maintaining steady stage conditions in the main fermentation stage, thereby producing a fermentation broth containing mevinolin. Preferably, the steady state conditions are maintained in the main fermentation stage by one or more of feeding of organic carbon sources; controlling glucose and/or total reducing sugar content; feeding of organic nitrogen sources; controlling pH; controlling foam level; controlling the mass of the fermentation broth by withdrawals and feedings; and, controlling the dissolved oxygen level.

20 Claims, No Drawings

METABOLIC CONTROLLED FERMENTATION PROCEDURE FOR THE MANUFACTURE OF LOVASTATIN HYDROXY ACID

FIELD OF THE INVENTION

This invention relates generally to the biosynthesis of cholesterol reducing agents. More specifically, the invention relates to the biosynthesis of the cholesterol lowering agent mevinolin by certain microorganisms.

BACKGROUND OF THE INVENTION

Mevinolin (lovastatin; monacolin K; β,δ-dihydroxy-7-[1,2,6,7,8,8a-hexahydro-2,6-dimethyl-8-(2-methyl-butyryloxy)-naphtalen-1-yl]-heptanoic acid δ-lactone) is one of the most important known cholesterol lowering agents. Mevinolin, as used herein, includes both the lactone and free hydroxy acid forms.

Its open hydroxy acid form is a potent inhibitor of the 3-hydroxy-3-methyl-glutarylcoenzyme A reductase enzyme, which catalyses the formation of mevalonic acid, an early intermediate of cholesterol biosynthesis. Mevinolin is specifically advantageous because, as a result of its application, biosynthetic intermediates with a toxic steroid skeleton, formed at a later stage of biosynthesis fail to accumulate. Mevinolin increases the number of LDL-receptors at the surface of the cell membrane which remove the LDL cholesterol circulating in the blood, thereby inducing the lowering of blood plasma cholesterol level.

Commonly, the active ingredient is produced via fermentation. GB 2046737 discloses that the active ingredient can be produced by some strains belonging to the Monascus genus e.g. by M. ruber 1005 cultivated between 7 and 40° C. As a culture medium the aqueous solution of glucose, peptone, corn steep liquor and ammonium chloride was used. The fermentation was carried out for 10 days in aerobic conditions, and 87 mg mevinolin was obtained from the filtrate of 5 liters broth.

U.S. Pat. No. 4,294,926 discloses the biosynthesis of the mevinolin preferably by the application of microorganisms under the deposited numbers ATCC 20541 or 20542 belonging to the *Aspergillus terreus* genus on a culture medium containing carbohydrates, e.g., glucose, fructose, maltose, as carbon source, nitrogen sources, e.g., yeast, hydrolyzed yeast, hydrolyzed casein, corn steep liquor; and mineral salts, e.g., calcium carbonate, magnesium sulphate, cobalt, ferro, manganic salts at a temperature of 20–37° C. Similar procedures are described in U.S. Pat. Nos. 4,420,491, 4,342,767, 4,319,039 and 4,294,846, where the fermentations are carried out for 3–5 days on media containing 1–6% carbohydrates and 0.2–6% nitrogen sources.

German Patent No. 4,402,591 discloses biosynthesis of mevinolin by microorganisms belonging to the Pleurotus genus, e.g., *Pleurotus ostreatus, P. sapidus, P. saca*, at 25–35° C. during 7–14 days cultivation time on surface or submerge cultures.

Canadian Patent No. 2,129,416 discloses the preparation of mevinolin, or in a particular case, mevastatin, with a microorganism belonging to the Coniothyrium genus, e.g., under the deposited number *Coniothyrium fuckelii* ATCC 74227 on a culture medium containing 3–15% glucose, 0.54% peptone, 0.5–5% amylase, 0.2–1% ammonium sulphate, 0.01–0.1% magnesium sulphate, 0.05–0.2% antifoaming agent, 0.2–1.5% L-isoleucine, 0.2–1.5% L-aspartic acid in the pH range of 5–6. According to the examples the active ingredient concentration of the broth was within 19–430 mg/liter.

Hungarian Patent No. HU 208,997 discloses the application of the holotype strain *Aspergillus obscurus* numbered as MV-1, deposited under the number NCAIM(P)F 001189. The fermentation is preferably carried out on a medium containing yeast extract and/or peptone and/or casein as nitrogen source(s) and glucose and/or maltose or sucrose as carbon source(s). The activity of the broth at the end of the laboratory scale cultivation is between 400–850 mg/liter.

The foregoing discussion establishes that the development work in the biosynthesis of mevinolin focused on discovery of new mevinolin-producing microorganisms rather than on the development of the fermentation procedure itself. Several references disclose that fermentations can be carried out on conventional and known media with the application of both surface and solid state cultivations. Batch-like procedures were applied, where the behaviors of the procedures depended on the initial conditions. However, technical limitations, e.g., maintaining the most convenient level of ingredients, optimal dissolved oxygen supply and pH, etc., made it difficult to implement continuous corrective actions to ensure more favourable conditions. A given microorganism during the main fermentation stage, depending on its metabolism, requires different conditions/composition of media in order to obtain an optimal growth and production of the active ingredient. The present inventors concluded from their experiments that in the seed culture and at the beginning of the main fermentation, the quantity of the active biomass is very small and variable. Thus, the yield of the fermentations are relatively low and variable. Yields reached at the end of the fermentations, which depended of course on the strain, did not exceed a mevinolin concentration of 850 mg/liter. The present inventors performed a detailed analysis of the whole fermentation procedure from the seed culture stage throughout the end of the fermentation. It was found that in the seed culture preparation stage, both in the case of the known media and execution processes, the quantity of the biomass is too low. Therefore, during the main fermentation, the metabolism of the microorganism and the culture are not adequate.

OBJECTS OF THE INVENTION

It is therefore, one object of the present invention is to improve the efficiency of the mevinolin-producing fermentation procedure by forcing the production ability of the microorganism via changing the conditions and the carrying out of the fermentations.

It is another object of the present invention to provide, in ether or both the seed and main fermentation stage, the most convenient chemical and physiological conditions for the metabolism by the microorganism.

It is a further object of the present invention to provide, in ether or both the seed and main fermentation stage, the most convenient chemical and physiological conditions for the metabolism by the microorganism by maintaining in a steady state condition, the growth rate and then, for an extended time, a maximal product formation rate.

SUMMARY OF THE INVENTION

These and other objects of the invention are achieved in one embodiment of the present invention by providing a method for producing mevinolin by microorganism in a fermentation process having a seed culture stage and a main fermentation stage, said method comprising:

a) cultivating a microorganism biomass in said seed culture stage to produce an inoculum;
b) transferring said inoculum into a fermentation medium in said main fermentation stage; and,
c) maintaining steady stage conditions in said main fermentation stage, thereby producing a fermentation broth containing mevinolin.

In a preferred embodiment of the present invention, steady state conditions are maintained in the main fermentation stage by one or more of feeding of organic carbon sources; controlling glucose and/or total reducing sugar content; feeding of organic and/or inorganic nitrogen sources; controlling pH; controlling foam level; controlling the mass of the fermentation broth by withdrawals and feedings; and, controlling the dissolved oxygen level. Preferably, the fermentation process in conducted in a submerged culture of the microorganism and at a temperature in the range of from about 24° C. to 30° C. In a particularly preferred embodiment of the present invention, the microorganism is an Aspergillus species. In yet other preferred embodiments of the present invention, the organic carbon source is selected from the group consisting of glucose, hydrolyzed starch and vegetable oil; the glucose content is maintained at bellow about 0.2% from the 60th hour of the main fermentation stage; the nitrogen sources are selected from the group consisting of corn steep liquor and ammonium hydroxide; pH is controlled to be within the range of from about 5.2 to about 7.0, preferably from about 5.2 to about 6.2, feeding carbon sources and/or base; foam level is controlled by addition of a material for controlling the foam level, the material preferably being a synthetic material or vegetable oil; and, dissolved oxygen level is controlled preferably by stirring and/or aeration of the fermentation broth. In yet another preferred embodiment of the present invention, the inoculum is transferred from the seed culture stage to the main fermentation stage when the pH of the seed culture stage is increasing after having reached its minimum value.

DETAILED DESCRIPTION OF THE INVENTION

The inventors have discovered that optimal biosynthesis of mevinolin may be performed by adjusting one or more of certain process parameters, steps and/or variables in ether or both the seed culture and main fermentation stages of the biosynthesis process.

During the seed culture phase, the inventors have found these process parameters, steps and/or variables to include supplying the microorganisms with the necessary medium components in easily assimilable form and in the most convenient concentration and, extending the cultivation time by about 10 to about 25%.

In order to obtain a steady state condition during the main fermentation stage, the inventors have found these process parameters, steps and/or variables to include controlling the glucose and/or the total reducing sugar content, maintaining the carbon sources at a suitable minimum level, feeding organic and/or inorganic nitrogen sources, controlling pH, controlling foam level, controlling the mass of the broth by withdrawals and feeding and controlling the dissolved oxygen level by changing the stirring rate and/or aeration rate.

In order to optimize mevinolin biosynthesis, it is not necessary that each of the above-mentioned process parameters, steps and/or variables for either the seed culture phase or for the main fermentation stage be simultaneously adjusted. However, in a preferred embodiment of the present invention, the biosynthesis of mevinolin will involve each of the above-mentioned process parameters, steps and/or variables. In such a preferred embodiment, an advanced metabolic controlled mevinolin fermentation procedure can be carried out in which a steady state condition, i.e. constant pH, glucose concentration, dissolved oxygen, viscosity, volume, etc., can be reached quickly and which can be maintained for a long time providing a yield highly exceeding the results of the known procedures.

Certain advantages may be realized in the seed culture stage by adjustment of one or more of the above-mentioned process parameters, steps and/or variables in that stage. These advantages include, e.g., reduction of the time requirement to reach the "steady state" condition by about 20–30% by increasing the number of growth centres and, growth of the active biomass in a more advantageous morphology form, resulting in more favourable conditions for cultivation of the microorganism. As a result of these advantages and the elongated cultivation time, the concentration of the active biomass is almost doubled.

Certain advantages may be realized in the main fermentation stage by adjustment of one or more of the above-mentioned process parameters, steps and/or variables in that stage. These advantages include, e.g., a faster and less fluctuating growth phase and quick formation of a steady state stage that can be maintained for a long time. These advantages result in a considerably increased activity of the fermentation.

Thus, in one embodiment, the present invention is directed to a fermentation procedure for the manufacture of mevinolin with a strain belonging to the Aspergillus genus in submerged culture at a pH between 5.2 and 7.0, at a temperature within 24 and 30° C., on a medium containing assimilable carbon and nitrogen sources, and mineral salts, wherein a metabolic controlled procedure is applied in the main fermentation phase in order to maintain the culture in a "steady state" stage. In this embodiment, the total reducing sugar is preferably controlled. In the source of the main fermentation, organic carbon sources, e.g., glucose, hydrolyzed starch and vegetable oil are preferably fed. Preferably, the glucose concentration level is maintained below 0.2% from the 60th hour of the fermentation. In the course of the procedure, nitrogen sources such as corn steep liquor and ammonium hydroxide solution are fed. The pH is preferably maintained in the range of from about 5.2–6.2 by feeding carbon source and/or base, e.g., ammonium hydroxide and/or sodium hydroxide. The foam level the fermenter may also be controlled by feeding vegetable oil, e.g., sunflower oil and/or soya bean oil, and/or synthetic antifoaming agent into the broth. Dissolved oxygen is preferably controlled changing the stirring rate and/or aeration rate. In the course of the fermentation, one or more withdrawals are carried out.

In a preferred embodiment, the main culture medium is inoculated by a seed culture having the following composition:

| Component | Amount (w/v %) |
| --- | --- |
| glucose | 2–6 |
| phosphoric acid | 0.002–0.006 |
| acidic casein | 0.2–0.8 |
| corn seep liquor | 1.5–5 |
| sunflower oil | 0.05–0.18 |
| polypropylene glycol | 0.05–0.18 |
| pancreatin* | 0.002–0.008 |

*4 times activity according to Ph.Hg.VII.

Culture medium with the above composition is completed with the regularly applied micro- and macroelemental salts, e.g., inorganic salts of sodium, potassium, magnesium and iron. The main culture medium is inoculated with a seed culture of which cultivation time is elongated by 10–25%. At the transferring stage of the seed culture the pH is in the increasing phase after its minimum value.

For the fermentation preferably the *Aspergillus obscurus* strain, its variant, or its mutant, or more preferably the *Aspergillus obscurus* n. sp. Mv-1 holotype strain deposited under the code number NCAIM(P)F 001189 is used.

The seed culture is inoculated into the sterile main fermentation medium with elongated cultivation time at the increasing phase of the pH after its minimum value. In the main fermentation stage, a "steady state" condition with the maximal active ingredient production rate can be maintained for a long time by feeding of the carbon and nitrogen sources in order to supply the nutrient demand; controlling the glucose concentration to avoid the undesirable thickening of the culture and the exaggerated increase in biomass; controlling the stirring rate and aeration rate according to the oxygen demand; combining foam level control with the carbon source demand an appropriate material for both purposes, e.g., a mixture of a vegetable oil and a synthetic agent; maintaining the pH between the range of from about 5.2–6.2 with the feeding of carbon source, e.g., glucose syrup, or base; and, carrying out one or more withdrawals, when the maximal working volume of the fermenter is achieved, or when a mevinolin concentration economical enough to carry out the downstream processing is reached.

By application of these elements, a versatile controllable fermentation procedure can be obtained, which depending on the life cycle is able to provide well-conditioned constant surroundings for the microorganism.

In accordance with the preferred embodiment described above, the present invention procedures yields exceeding those of known procedures, uses considerably less raw material and energy, reduces the quantity of environmentally polluting waste material relative to the unit mass of active material, and better utilizes the fermenter.

In the following Examples, biosynthesis of mevinolin in accordance with the process disclosed in HU 208997 (Comparative Example 1) is compared with the process in accordance with a preferred embodiment of the present invention (Example 2).

Comparative Example 1

Biosynthesis of Mevinolin in Accordance with HU 208997

A seed culture medium having the following composition is prepared in a 600 liter vessel:

| Component | Amount (%) |
| --- | --- |
| glucose | 4.0 |
| casein peptone | 0.5 |
| NaNO$_3$ | 0.3 |
| KH$_2$PO$_4$ | 0.2 |
| KCl | 0.05 |
| MgSO$_4$*7H$_2$O | 0.05 |
| FeSO$_4$*7H$_2$O | 0.001 |

Seeding of the inoculum was carried out by the spore suspension of the *Aspergillus obscurus* strain with spore number of 6.5×10$^9$. Process parameters of the seed culture were as follows:

| Parameter | Value |
| --- | --- |
| Volume | 400 liters |
| Temperature | 27° C. |
| Aeration Rate | 20 Normal m$^3$/h |
| Internal Pressure: | 0.5 bar |
| Stirring Rate: | 320 rpm |

Transferring of the seed culture into the main fermentation medium is done according to the standard procedure at the age of 36 hour, when the pH was in its decreasing stage at 5.6. Centrifuged packed cell volume of the biomass (PCV) was 14%.

The above seed culture was inoculated into the main fermentation medium labeled MEF-03 at 10% inoculation rate. The composition of the main fermentation medium was as follows:

| Component | Amount (%) |
| --- | --- |
| Dextrose Monohydrate | 1.0 |
| Acidic Casein | 0.2 |
| Corn Starch | 8 |
| Soya Bean Meal | 1.5 |
| Corn Steep Liquor (50%) | 1 |
| Sodium Chloride | 1 |
| Potassium Dihydrogen Phosphate | 0.2 |
| Sodium Glutamate | 1.2 |
| Sunflower Oil | 0.16 |
| Polypropyleneglycol | 0.16 |
| Pancreatine* | 0.002 |
| BAN 240 Enzyme | 0.007 |
| CaCl$_2$ | 0.02 |
| Potassium Hydroxide | for pH setting |

*4 times strength according to Ph.Hg.VII.

Volume at 0 hour: 500 liters.

The fermentation is carried out for 7 days. The aeration and stirring rates are as follows:

| Aeration* | Stirring rate* |
| --- | --- |
| 18–25 Normal m$^3$/h | 180–320 rpm |

*Dissolved oxygen is maintained above 40% of the saturation value.

During the course of the fermentation, four 50 kg portions enzymatically liquefied corn starch is fed according to a schedule at the age of 50, 73, 90 and 108 hours.

Data for the Active Ingredient Production

Fermentation time: 164 hours. Activity measured by HPLC: 927 mg/kg. Quantity of the broth: 580 kg. As a consequence of the above, the quantity of the fermented active ingredient is 0.58 ton*927 g/ton/1000/1 m$^3$=0.54 kg/m$^3$ total volume.

EXAMPLE 2

Biosynthesis of Mevinolin with Glucose Syrup and Nitrogen Source Feeding and pH Control by Sodium Hydroxide or Ammonium Hydroxide In a 600 liter vessel is prepared a seed culture medium having the following composition:

| Component | % |
| --- | --- |
| glucose | 4.0 |
| casein peptone | 0.5 |
| corn steep liquor (50%) | 3.0 |
| NaNO$_3$ | 0.3 |
| KH$_2$PO$_4$ | 0.2 |
| KCl | 0.05 |
| MgSO$_4$*7H$_2$O | 0.05 |
| FeSO$_4$*7H$_2$O | 0.001 |
| pancreatine* | 0.005 |
| polypropyleneglycol | 0.1 |
| sunflower oil | 0.1 |

*4 times strength according to Ph.Hg.VII.

Seeding was done by the spore suspension of the *Aspergillus obscurus* strain with spore number of 6.5×10$^9$. Process parameters of the seed culture were the same as set forth in Comparative Example 1.

However, transferring of the seed culture was done differently from the transferring described in Comparative Example 1. The age of transferring was 40 hours. The pH reached a minimum value (pH 4.9), and the transferring was in the stage when the pH had started to increase and reached about 5.0. Thus, the pH had increased about 0.1 from its minimum value. The centrifuged packed cell volume of the biomass (PCV) was 24%.

The above seed culture was inoculated into the main fermentation medium at a 10% inoculation rate. The composition of the main fermentation medium was the following:

| Component | Amount(%) |
| --- | --- |
| corn starch | 8 |
| glucose syrup* | 1.0 |
| acidic casein | 0.2 |
| soya bean meal | 1.5 |
| corn steep liquor (50%) | 1 |
| sodium chloride | 1 |
| potassium dihydrogen phosphate | 0.2 |
| sodium glutamate | 1.2 |
| sunflower oil | 0.16 |
| polypropyleneglycol | 0.16 |
| pancreatine** | 0.002 |
| potassium hydroxide | for pH setting |

*25 kg was fed in the form of 25% glucose syrup
**4 times strength according to Ph.Hg.VII.

Fermentation was carried out for 13 days. The aeration and stirring rates are as follows:

| Aeration* | Stirring rate* |
| --- | --- |
| min. 12, max. 32 Normal m$^3$/h | min. 220, max. 400 RPM |

*Dissolved oxygen was maintained above 40% of the saturation value by aeration priority method.

In the course of the fermentation, the maintenance of the dissolved oxygen is very important. In the most intensive stage, this can be reached by the application of about 25–32 Normal m$^3$/h aeration rate and 300–400 RPM stirring rate.

During the main fermentation stage, the temperature was 27±2° C., the inner pressure was 0.4 bar, and the cultivation time was 309 hours.

In the course of the fermentation, the following nutrients were fed:

1. Hydrolyzed corn starch (glucose syrup) is prepared with enzymatic and hydrochloric acid treatment and fed. The raw materials used to prepare the glucose syrup were as follows: 25% corn starch, 0.3–0.4% CaCl$_2$, 0.1–0.2% amylase enzyme (BAN) and, 1% concentrated hydrochloric acid. Feeding of the glucose syrup started in the increasing stage of the pH, after its minimum value (5.0) in the age of 45 hours and at the pH value of 5.6. Feeding was carried out in a continuously, maintaining the pH in the range of 5.4 and 5.8. The minimum rate of feeding was 0.5 liter/hour and the maximal rate of feeding was 5 liter/hour.

2. NaOH or NH$_4$OH solution was feed for pH control when the pH dropped below 5.5 in addition to the minimum feeding rate of the glucose syrup.

3. Corn seep liquor (1%) was fed at the age of 100 hours of the fermentation (related to the 0 hour volume).

Data for the Active Ingredient Production

Fermentation time: 309 hours. Activity measured by HPLC: 2868 mg/kg. Quantity of the broth: 680 kg. As a consequence of the above, the quantity of the fermented active ingredient is 0.68 ton*2868 g/ton/1000/1 m$^3$=1.95 kg/m$^3$ total volume.

EXAMPLE 3

Biosynthesis of Mevinolin with Feedings, Controlling and Withdrawals

*Aspergillus obscurus* n. sp. MV-1 holotype strain is cultivated on a sterile inoculum medium with the following composition:

| Component | % |
| --- | --- |
| glucose | 4.0 |
| phosphoric acid | 0.0035 |
| acidic casein | 0.5 |
| corn steep liquor (50%) | 3.0 |
| NaNO$_3$ | 0.3 |
| KH$_2$PO$_4$ | 0.2 |
| KCl | 0.05 |
| MgSO$_4$*7H$_2$O | 0.05 |
| FeSO$_4$*7H$_2$O | 0.001 |
| sunflower oil | 0.1 |
| polypropylene glycol | 0.1 |
| pancreatine* | 0.005 |
| potassium hydroxide | for pH setting |
| hydrochloric acid | for pH setting |

*4 times strength according to Ph.Hg.VII.

The following process parameters were employed during the inoculum stage:

| Parameter | Value |
| --- | --- |
| Volume | 8 m$^3$ |
| Stirring rate | 120 RPM |
| Aeration | 400 ± 50 Normal m$^3$/h |
| Inner pressure | 0.4 ± 0.1 bar |
| Temperature | 27 ± 2 ° C. |

The inoculum was transferred after its pH had reached its minimum value (pH 4.8) and when the value was 0.1 unit above the minimum, i.e. when the pH had reached a value of 4.9. The centrifuged packed cell volume of the biomass (PCV) was 24%. At an 8% transfer rate, the above inoculum was transferred into a main fermentation medium having the following composition:

| Component | Amount (%) |
| --- | --- |
| Soya bean meal | 1.28–1.57 |
| sum of corn or wheat starch | 9 |
| acidic casein | 0.20 |
| corn steep liquor (50%) | 0.857–1.14 |
| sodium chloride | 1.0 |
| potassium dihydrogen phosphate | 0.2 |
| sodium glutamate | 1.14–1.20 |
| calcium chloride | $3.8 \times 10^{-3}$ |
| BAN enzyme | $2.2 \times 10^{-3}$ |
| sunflower oil | 0.10 |
| polypropyleneglycol | 0.10 |
| pancreatine* | $2.0 \times 10^{-3}$ |
| potassium hydroxide or hydrochloric acid | for pH setting |

*4 times strength according to Ph.Hg.VII.

The following process parameters were employed during the main fermentation stage:

| Parameter | Value |
| --- | --- |
| Inner pressure | $0.2 \pm 0.05$ bar |
| Temperature | $27 \pm 2$ °C. |
| Stirring rate | 60–85 RPM |
| Aeration rate | 1000–4000 Normal $m^3/h$ |

Feeding Materials
1. Carbon source material: About 40 ton hydrolyzed starch, degraded to a large extent until glucose (glucose syrup) is prepared in 25% form is fed continuously. The raw materials used to prepare the glucose syrup are as follows: 25% corn or wheat starch, 0.3 calcium chloride, 0.3% BAN 240 enzyme and about 2% hydrochloric acid.
2. Nitrogen source material: Corn steep liquor (50%) is used for the preparation in 1% quantity related to 0 hour fermentation volume in 5 $m^3$ sterile volume.
3. Base for pH control. Unsterilized 25–30% sodium hydroxide or ammonia solution is used for pH control.

Feeding
1. Glucose syrup: Feeding is started at about 50 hours in the increasing stage of the pH after its first minimum value. Glucose syrup is fed in order to control the pH in the range of 5.4 and 5.8. Glucose feeding is carried out in dose form or continuously. The glucose syrup is fed at a rate in the range of 0–1000 kg/hour, preferably in the range of 150–500 kg/hour. When the pH minimum could not be maintained, even with the minimum glucose syrup feeding rate, base feeding was necessary to control pH.
2. Corn steep liquor: The corn steep liquor is fed in one dose at about 100 hour. Further doses could be fed if necessary.
3. NaOH or $NH_4OH$: The base was fed and pH control was performed when, in addition to the minimum glucose syrup feeding rate, the pH dropped bellow 5.5.

The foam level is controlled by the feeding of the mixture of sunflower oil:PPG in the rate of 95:5 in order not to exceed a foam volume of 25% of the fermenter working volume.

Withdrawals were carried out from the fermenter at the ages of 112, 138, 178, 204 hours by harvesting 4 $m^3$ broth 4 times.

Data for the Active Ingredient Production

Fermentation time: 226 hours. Activity measured by HPLC (mother part): 1825 mg/kg. Harvested activity (with withdrawals): 1788 mg/kg. As a consequence of the above, the quantity of the fermented active ingredient is 95 ton*1788 g/ton/1000/105 $m^3$ total volume.

What is claimed is:

1. A fermentation procedure for the manufacture of lovastatin with a strain belonging to the Aspergillus genus in submerged culture at a pH between 5.2 and 7.0, at a temperature within 24 and 30° C., on a medium containing assimilable carbon and nitogen sources, and mineral salts, comprising a seed culture stage and a main fermentation stage wherein a metabolic controlled procedure is applied in the main fermentation stage in order to maintain the culture in a steady state.
2. A process of claim 1, wherein the metabolic controlled procedure comprises controlling total reducing sugar content during the main fermentation stage.
3. A process of claim 1, wherein organic nitrogen source is fed in the course of the main fermentation phase.
4. A process of claim 3, wherein as a carbon source glucose is fed.
5. A process of claim 4, wherein the glucose content is controlled by feeding from the age of 60 hours till the end of the fermentation below 0.2%.
6. A process of claim 3, wherein as a carbon source hydrolysed starch and/or vegetable oil are fed.
7. A process of claim 1, wherein nitrogen source is fed in the course of the main fermentation phase.
8. A process of claim 7, wherein as a nitrogen source corn steep liquor and/or ammonium hydroxide are fed.
9. A process of claim 1, wherein the pH is controlled in the course of the main fermentation phase between 5.2 and 6.2.
10. A process of claim 9, wherein the pH control is done by the carbon source and/or base feeding.
11. A process of claim 10, wherein ammonium hydroxide is used for base feeding.
12. A process of claim 1, further comprising a step of controlling foam formation.
13. A process of claim 12, wherein the foam control is done by vegetable oil and synthetic agent.
14. A process of claim 13, wherein the vegetable oil is sunflower oil and/or Soya bean oil.
15. A process of claim 1, wherein the stirring rate and/or aeration rate are controlled according to the dissolved oxygen level.
16. A process of claim 1, wherein partial harvests are done in the course of the main fermentation phase.
17. A process of claim 1, wherein the inoculation of the main fermentation phase is done by the Aspergillus microorganism culture cultivated on the following seed culture medium:

| | |
| --- | --- |
| glucose | 2–6 w/v % |
| phosphoric acid | 0.002–0.006 w/v % |
| acid casein | 0.2–0.8 w/v % |
| corn seep liquor, 50% | 1.5–5 w/v % |
| sunflower oil | 0.05–0.18 w/v |
| polypropylene glycol | 0.002–0.008 w/v % | pancreatin, 4 times activity according to Ph.Hg. VII completed with water and the regularly applied micro- and macroelemental salts.

18. A process of claim 1, wherein the transfer of the seed culture into the main fermentation is carried out by the application of the 10–25% elongated cultivation time related to the regular one and/or in the increasing phase of the pH after its minimum value.
19. A process of claim 1, wherein the applied microorganism is *Aspergillus obscurus*.
20. A process of claim 19, wherein the applied microorganism for the fermentation is the *Aspergillus obscurus* n. sp. MV-1 holotype strain deposited under the code number NCAIM(P)F 001189.

* * * * *